United States Patent [19]
Booth

[11] Patent Number: 5,976,095
[45] Date of Patent: Nov. 2, 1999

[54] NONINVASIVE BLOOD PRESSURE SLING

[75] Inventor: John Booth, Tampa, Fla.

[73] Assignee: Critikon Company, L.L.C., Tampa, Fla.

[21] Appl. No.: 09/001,181

[22] Filed: Dec. 30, 1997

[51] Int. Cl.[6] ....................................................... A61B 5/02
[52] U.S. Cl. .......................... 600/490; 600/485; 600/499
[58] Field of Search ............................ 600/485, 490–492, 600/499; 606/201–202

[56] References Cited

U.S. PATENT DOCUMENTS

| | | | |
|---|---|---|---|
| 4,315,504 | 2/1982 | Drennan et al. | 128/149 |
| 4,349,034 | 9/1982 | Ramsey, III | 128/681 |
| 4,360,029 | 11/1982 | Ramsey, III | 128/681 |
| 4,790,325 | 12/1988 | Lee | 128/677 |
| 4,922,929 | 5/1990 | DeJournett | 128/892 |
| 5,094,244 | 3/1992 | Callahan et al. | 600/499 |
| 5,454,831 | 10/1995 | McEwen | 600/485 |
| 5,595,180 | 1/1997 | Ogura et al. | 600/499 |

*Primary Examiner*—Cary O'Connor
*Assistant Examiner*—Ryan Carter
*Attorney, Agent, or Firm*—Woodcock Washburn Kurtz Mackiewicz & Norris LLP

[57] ABSTRACT

A sling for use with a noninvasive blood pressure monitor which is designed to minimize contact by external objects with an inflatable cuff which surrounds a patient's limb during blood pressure measurements. The sling comprises an arm rest having supporting straps for supporting the patient's limb at at least two locations so as to define an unsupported space therebetween adapted to accept the inflatable cuff such that the inflatable cuff does not touch the straps or external objects. Preferably, the sling comprises two braces having bottom surfaces to serve as a base for the sling, linking members having ends which are attached to the braces so that the linking members extend between the braces, and two supporting straps, attached to and extending between two linking members, for supporting the patient's arm. The straps are positioned adjacent the braces so that a gap is provided between the straps for placement of the inflatable cuff such that the inflatable cuff does not touch the straps or external objects. The linking members are adjustable to accommodate patients' arms of various sizes. The components of the sling may be made completely out of foam material, so long as an opening for the blood pressure cuff is provided.

16 Claims, 5 Drawing Sheets

NONINVASIVE BLOOD PRESSURE SLING

FIELD OF THE INVENTION

This invention relates to a sling for use by a patient during automated blood pressure monitoring.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology.

In accordance with the Ramsey patents, an inflatable cuff is suitably located on the limb of a patient and is pumped to a predetermined pressure above the systolic pressure. Then, the cuff pressure is reduced in predetermined decrements, and at each level, pressure fluctuations are monitored. The resultant signals typically consist of a DC voltage with a small superimposed variational component caused by arterial blood pressure pulsations (referred to herein as "oscillation complexes" or just simply "oscillations").

After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter decrease. These amplitudes thus form an oscillometric blood pressure envelope for the patient. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator sets a time interval, typically from 1 to 90 minutes, at which blood pressure measurements are to be made.

The noninvasive blood pressure ("NIBP") monitor automatically starts a blood pressure determination at the end of the set time interval. Typically, the user selects a short interval if the patient is unstable because blood pressure may change to dangerous levels in a short time and selects a longer interval as the patient becomes more stable. The reason a short interval is not used in all cases is that the probability of trauma to the limb from the cuff inflation increases as the determination frequency increases.

U.S. Pat. No. 5,606,977, to Maynard Ramsey, III and commonly assigned herewith, employs the oscillometric methodology. This patent describes an automated sphygmomanometer which automatically determines when a blood pressure determination needs to be made and automatically determines whether the patient's blood pressure has changed significantly since the last determination so that a new blood pressure determination may be instigated immediately. This patent also discloses a technique for monitoring the status of the patient's blood pressure between determinations so that a change in status between blood pressure determinations will not go undetected. In addition, this invention discloses a technique for monitoring the status of the patient's blood pressure so that full blood pressure determinations need not be taken as frequently, thereby minimizing the possibility of trauma to the patient.

Automated NIBP techniques are normally utilized when constant monitoring of the patient's blood pressure is desired such as during surgeries, less serious medical procedures, or in ambulances on the way to a hospital. Thus, the accuracy of the PPA readings, the resulting MAP, and systolic and diastolic calculations are critical to the success of the procedure and the health of the patient.

It is, therefore, imperative that the oscillation complexes are rue representations of the patient's blood pressure. Patient movement, however, creates noise which interferes with accurate measurement of oscillation complexes using an inflatable blood pressure cuff. In particular, noise is caused when movement of the patient's arm causes the inflatable blood pressure cuff to contact an external object, thereby compressing the cuff between the object and the patient's arm. Such noise is particularly problematic in an ambulance or in an emergency room environment. This contact and resulting compression creates a noise pressure signal which interferes with accurate measurement and monitoring of the oscillation complexes. The noise will sometimes occur at the same time as an oscillation complex, and therefore, may be very difficult to discount as noise. Depending on the severity of contact, such noise can be mistaken for an oscillation complex.

Of course, devices are known that provide support to a patient's limb. U.S. Pat. No. 4,315,504, entitled "Elbow Suspension Device," describes such a device for bed and ambulatory patients which provides support above and below the elbow, thus protecting the elbow. U.S. Pat. No. 4,922,929, entitled "Padded Elbow Brace," describes such a device for protecting limb joints with cushioning material. U.S. Pat. No. 4,790,325, entitled "Automatic Arterial Blood Pressure Recorder," describes such a device which utilizes an arm rest built into the arm rest of a chair. The disclosed arm rest provides an ergonomic fit for the patient's arm and serves to position the arm so that automatic blood pressure monitoring can be performed. However, an obvious problematic feature of this device is that the arm rest is in direct contact with the inflatable blood pressure cuff, leading to interference from noise.

At a minimum, noise caused when the inflatable cuff contacts external objects interferes with accurate blood pressure measurement. It is, accordingly, an object of the present invention to reduce the amount of noise that interferes with accurate blood pressure measurement and monitoring with automated noninvasive blood pressure devices by providing a device which minimizes cuff contact with external objects during such measurement.

SUMMARY OF THE INVENTION

A sling for use with a noninvasive blood pressure monitor is designed to minimize contact by external objects with an inflatable cuff which surrounds a patient's limb during a blood pressure measurement. The sling comprises an arm rest having supporting surfaces for supporting the patient's limb at at least two locations so as to define an unsupported space therebetween adapted to accept the inflatable cuff such that the inflatable cuff does not touch the supporting surfaces or external objects.

A preferred embodiment of the invention comprises two braces having bottom surfaces to serve as a base for the sling, two linking members having ends which are attached to the braces so that the linking members extend between the braces, and two supporting straps, attached to and extending between the two linking members, for supporting the patient's arm. The straps are positioned adjacent the braces so that a gap is provided between the straps for placement of the inflatable cuff such that the inflatable cuff does not touch the straps, the linking members, or external objects.

Preferably, the linking members are telescopic so that the sling may be adjusted to accommodate patients' arms of varying sizes. In a preferred embodiment, two upper linking members and two lower linking members are provided, wherein the supporting straps are attached to the two upper linking members so that the straps do not interfere or come in contact with the inflatable cuff. The supporting straps may further comprise extensions so that the straps completely surround the patient's arm to help immobilize the patient's arm. These extensions are preferably attached to the patient's arm using VELCRO™ and the like.

In another embodiment of the invention, the sling comprises two supporting members which serve as bases for the sling and as supports for the patient's arm. The supporting members are positioned so that a gap is provided between the supporting members for placement of the inflatable cuff such that the inflatable cuff does not touch the supporting members or any external objects. One or more adjustable linking members having ends which are attached to the supporting members are provided so that the gap between the supporting members may be adjusted to accept arms of different sizes. Preferably, the supporting members comprise blocks made of a foam material. Alternatively, the blocks and the linking members are made of one integral piece of foam material.

A method of measuring blood pressure of a patient using a noninvasive blood pressure monitor and a sling according to the present invention is also provided comprising the steps of: 1) resting the patient's arm on the sling so that an upper portion of the patient's arm is situated in unsupported space free from contact with the sling, b) applying the inflatable cuff on the upper portion of the patient's arm so that the inflatable cuff does not touch the straps or external objects, and c) taking blood pressure measurements.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PREFERRED EMBODIMENTS

A system and method which meets the above-mentioned objects and provides other beneficial features in accordance with the presently preferred exemplary embodiment of the invention will be described below with reference to FIGS. 1–5. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

Figure 1:
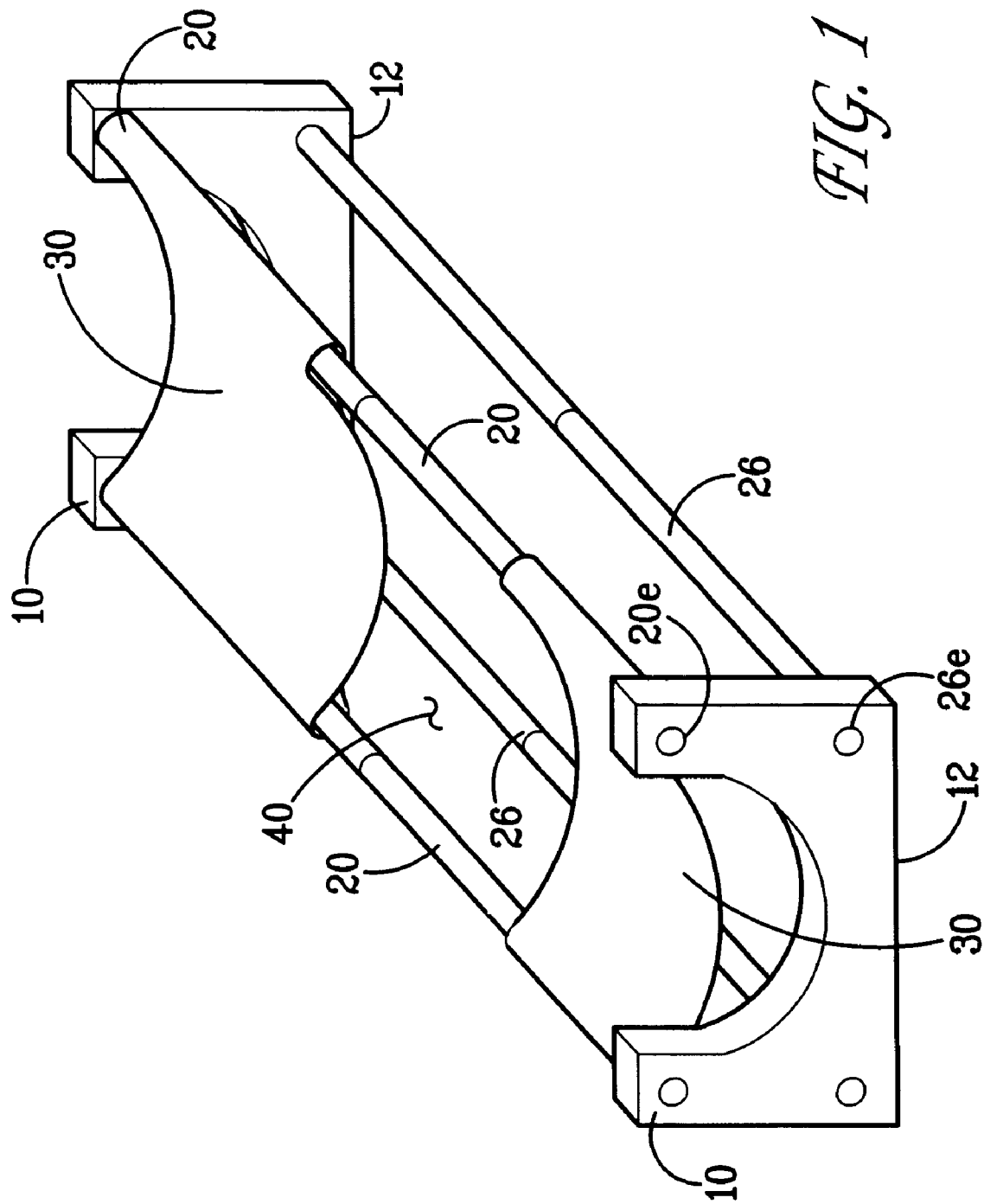
FIG. 1 is a perspective view of a preferred embodiment of a noninvasive blood pressure sling according to the present invention.

FIG. 1 shows a perspective view of a preferred embodiment of a noninvasive blood pressure sling according to the present invention. This preferred embodiment of the sling comprises two braces 10, two upper linking members 20 and two lower linking members 26 which extend between the braces 10, and two straps 30 extending between the two upper linking members 20 for supporting the patient's limb, typically the upper arm.

The two braces 10 hold the components of the sling together. The flat bottom surfaces 12 of the braces 10 serve as a base for the sling so that the sling and the patient's arm are kept steady during blood pressure monitoring. It is contemplated that the lower linking members 26 will also serve as a base for the sling, adding to its stability.

The linking members 20 and 26 are preferably telescoping rods which make the sling adjustable to accommodate patients' arms of various sizes. The telescoping rods 20 and 26 extend between the braces 10 and are attached at their ends 20E and 26E to the braces 10. The telescoping rods 20 and 26 are preferably hollow cylindrical tubes encircling a rod, upon which the tubes can move for adjusting the sling to desired sizes. Although four telescoping rods 20 and 26 having circular cross sections are shown in FIG. 1, other shapes and/or numbers of telescoping members are contemplated.

The two straps 30 extend between the two upper rods 20 for supporting the patient's arm. The supporting straps 30 are attached to the upper rods 20 and preferably made of a flexible material to comfortably support the patient's arm. The braces 10 are shaped so that the patient's arm does not make contact with the braces 10. The straps 30 are also positioned adjacent the braces 10, i.e., on the ends of the sling at the ends 20E of the upper telescoping rods 20. This positioning of straps 30 results in an open space 40 in the sling so that the straps 30 do not interfere or come in contact with the inflatable cuff of the automated noninvasive blood pressure ("NIBP") device. In this way, the telescoping rods 20 and 26 also serve to shield the inflatable cuff from contact with external objects or components of the sling itself. The primary advantage of the sling of the present invention is that it is an arm rest that minimizes contact between the inflatable cuff and external objects or components of the sling itself. Thus, by protecting and isolating the inflatable cuff in the gap 40 and promoting immobilization of the patient's arm, the NIBP sling of the present invention helps reduce the amount of noise that can occur in noninvasive blood pressure monitoring.

Figure 2:
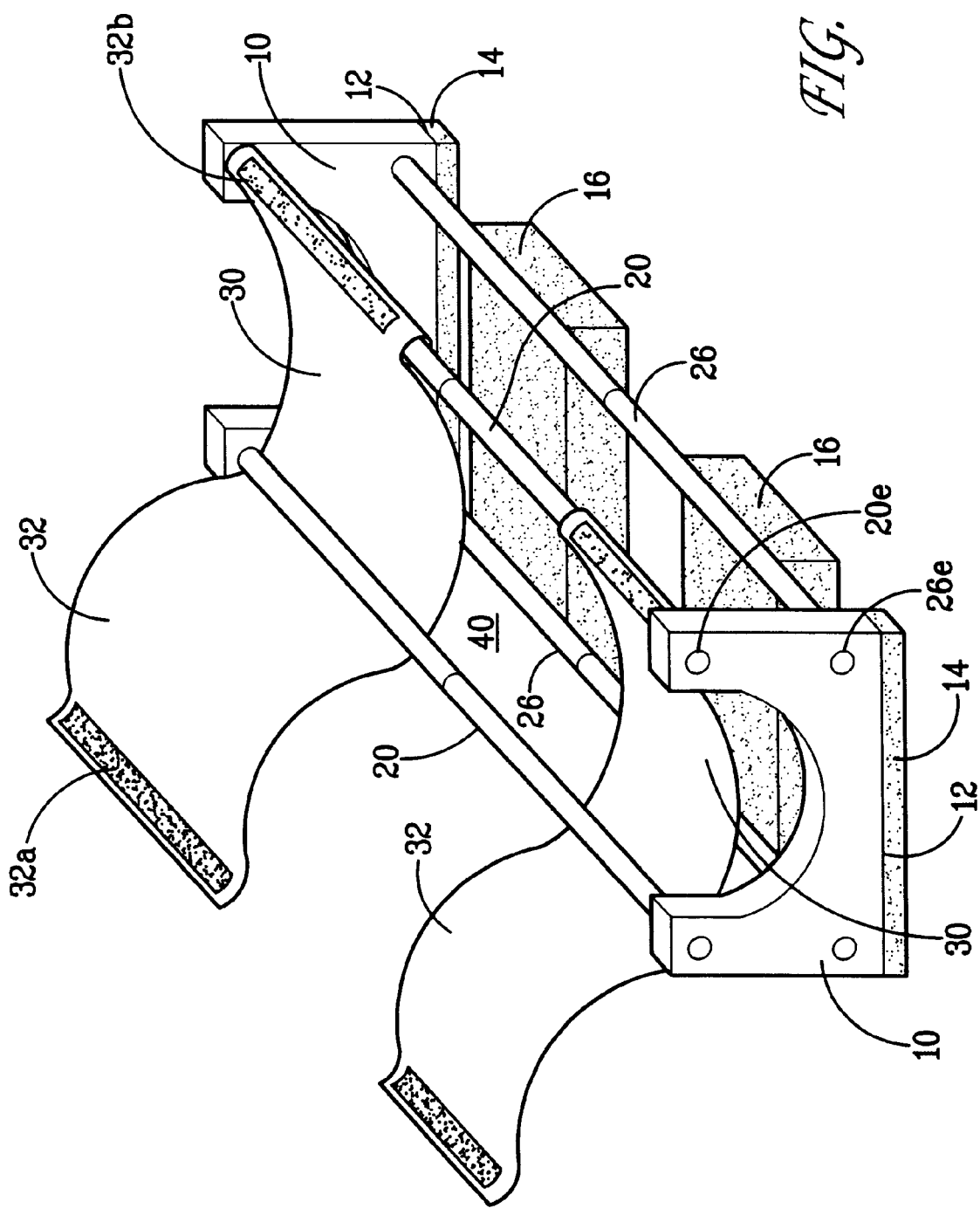
FIG. 2 is a perspective view of the embodiment of FIG. 1 modified to include attaching straps and shock absorbing foam.

FIG. 2 shows additional features of the present invention, which are contemplated in other embodiments of the NIBP sling. The flat bottom surfaces 12 of the braces 10 are covered with a shock-absorbing material 14 to further keep the patient's arm steady during blood pressure monitoring. For the same reason, shock-absorbing material 16 is placed underneath and attached to the lower telescoping rods 26. This dampening mechanism or cushioning is especially helpful in blood pressure monitoring during an ambulance ride to the hospital where an inherently bumpy ride can interfere with accurate blood pressure measurement and result in increased chances of noise.

Figure 3:
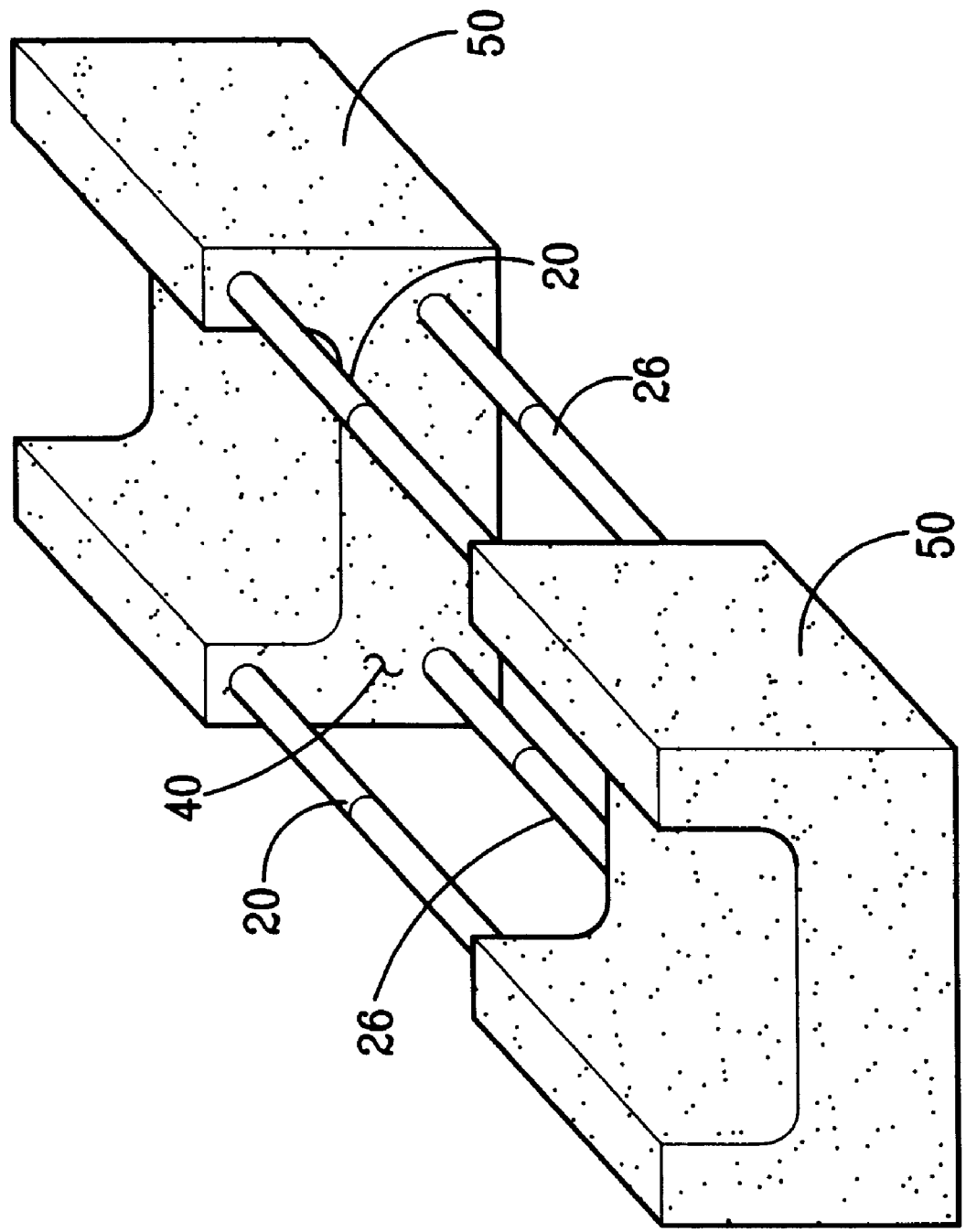
FIG. 3 is a perspective view of another alternate embodiment of a noninvasive blood pressure sling according to the present invention.
Figure 4:
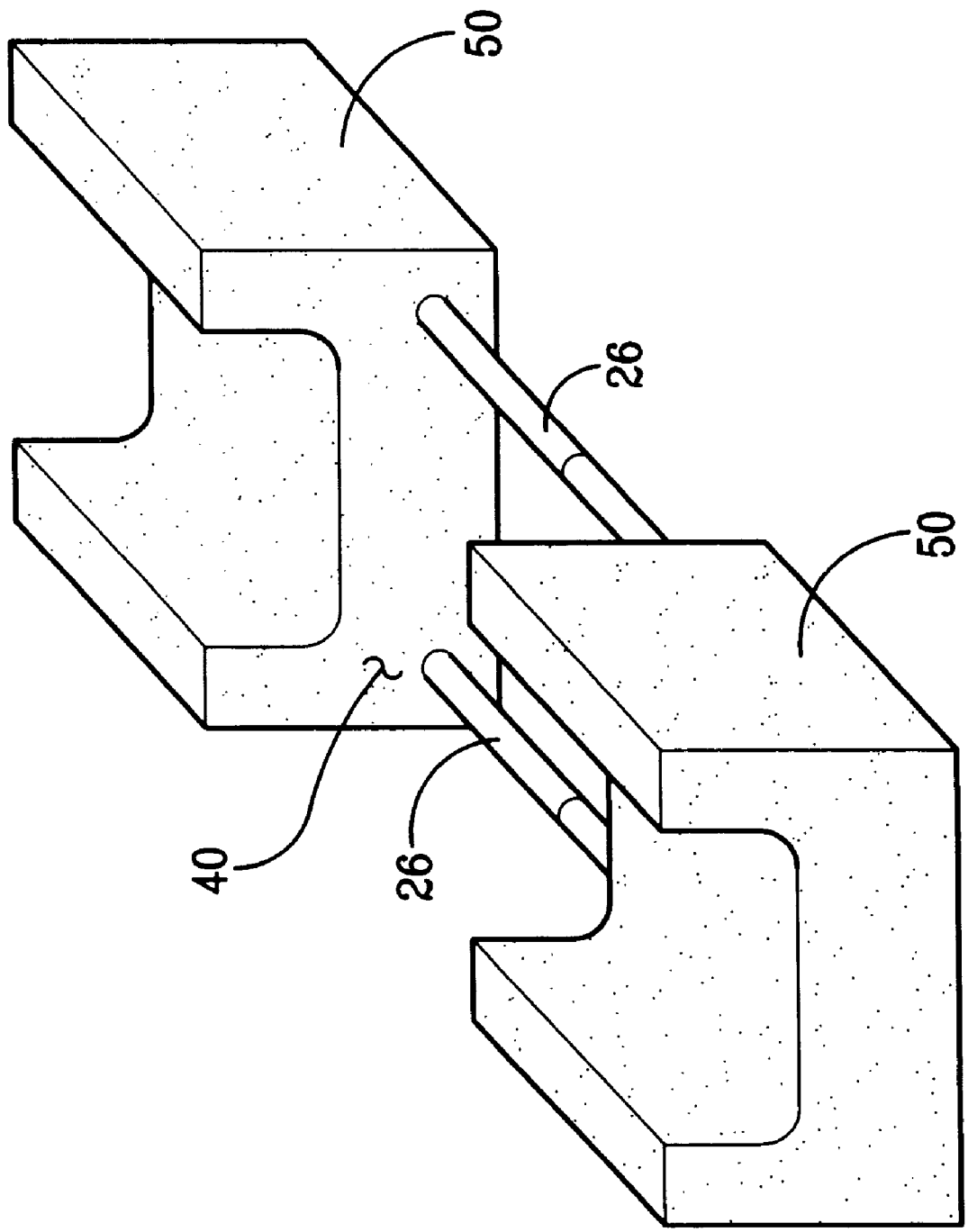
FIG. 4 is a perspective view of the embodiment of FIG. 3 with two instead of four linking members.
Figure 5:
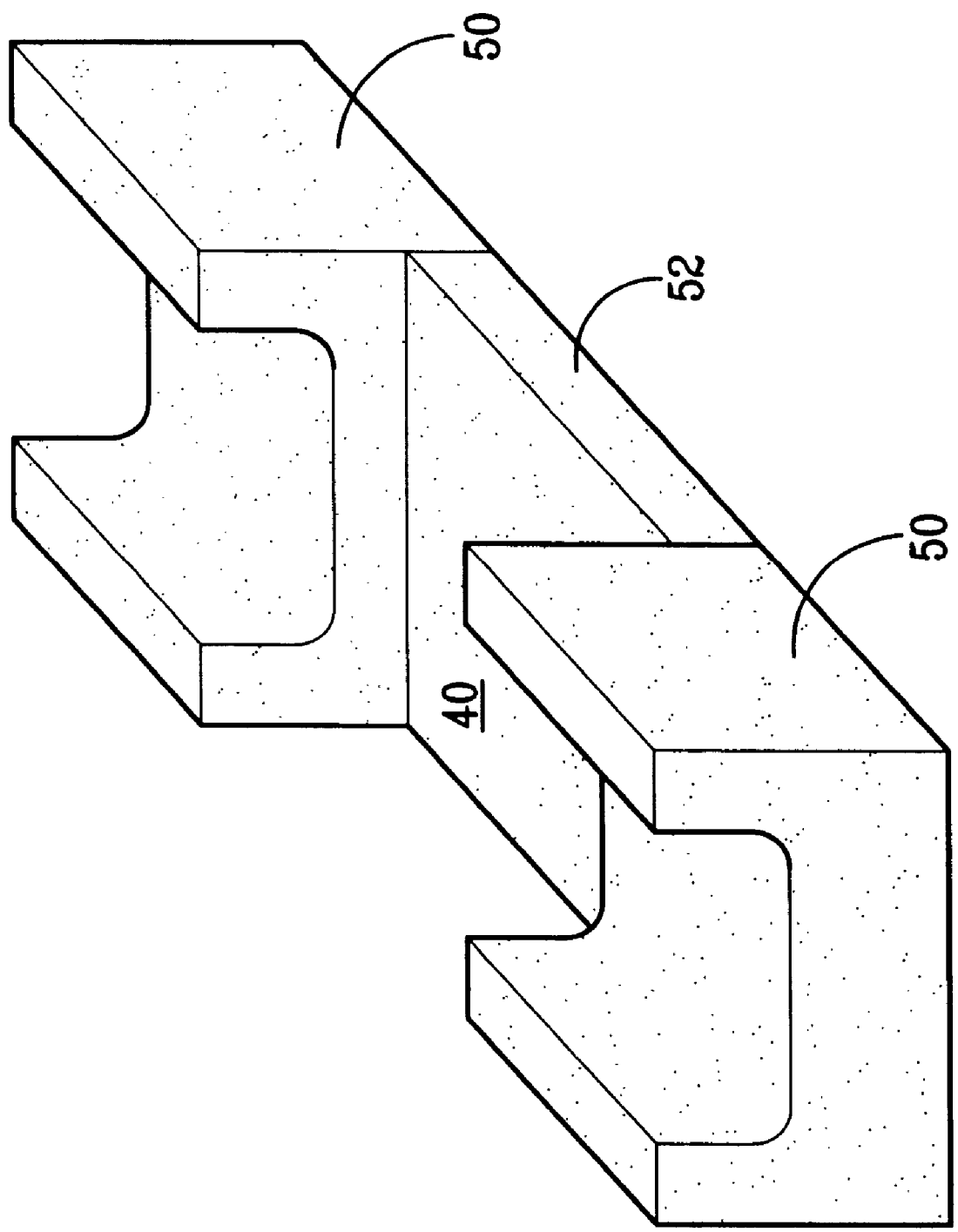
FIG. 5 is a perspective view of yet another alternate embodiment of a noninvasive blood pressure sling according to the present invention.

By reducing the chances of movement of the patient's arm, this cushioning 14 will also aid in reducing the chances of contact between the inflatable cuff and external objects or components of the sling itself. An extension of this cushioning idea is to manufacture other components of the sling or the entire sling out of shock-absorbing materials. For example, the braces 10, straps 30 and/or rods 20 and 26 may be replaced with components made completely out of foam material such as Styrofoam, so long as an opening (or gap 40) for the blood pressure cuff is provided. FIG. 3 shows an embodiment of the present invention in which the braces 10 and the straps 30 are replaced with foam blocks 50. Alternatively, the rods 20 may be removed as shown in FIG. 4, or the blocks 50 can be connected by a foam extension 52 as shown in FIG. 5 whereby the entire sling may be made of one integral piece of foam material. Such foam material in any of the embodiments of FIGS. 3–5 will further dampen out any vibrations before they reach the patient's arm. Also, to increase durability of the sling, the foam materials may include internal steel rods and the like to provide strength and rigidity.

There are also additional ways to further restrict movement of the patient's arm. For example, as shown in FIG. 2, the straps 30 of the present invention can completely surround the patient's arm and be bound to the art loosely enough so as not to interfere with accurate blood pressure measurements. Extensions 32 of the straps 30 on one side are folded over the patient's arm and attached to the other side by a simple attaching means 32A and 32B such as VELCRO™, thereby enclosing the patient's arm in the straps 30. This will further promote immobilization of the patient's arm and thereby further reduce the occurrence of noise caused from contact between the inflatable cuff and external objects or components of the sling itself. Such straps may be used with any of the sling embodiments described herein.

It will be appreciated by those skilled in the art that even though numerous characteristics and advantages of the present invention have been set forth in the foregoing description, together with details of the structure and function of the invention, the disclosure is illustrative only and numerous alternate embodiments are possible without departing from the novel teachings of the invention. For example, the telescoping rods of the invention may be replaced by a single slide plate, a single telescoping rod, or any other known mechanical extension device. Also, telescoping rods 26 in FIGS. 1–3 may be replaced by respective supporting portions for supporting the straps 30 but which do not extend through the gap 40. Instead, these supporting portions may be connected by a extensions extended downward to connect to linking members 26 so as to provide the required rigidity and support. In addition, modifications may be made in detail, especially in matters of shape, size and arrangement of parts within the principles of the invention to the full extent indicated by the broad general meaning of the terms in which the appended claims are expressed.

I claim:

1. A sling for use with a noninvasive blood pressure monitor to minimize contact by external objects with an inflatable cuff which surrounds a patient's limb during a blood pressure measurement, comprising an arm rest having supporting surfaces for supporting the patient's limb at at least two locations so as to define an unsupported space therebetween adapted to accept said inflatable cuff such that said inflatable cuff does not touch said supporting surfaces or said external objects.

2. A sling for use with a noninvasive blood pressure monitor to minimize contact by external objects with an inflatable cuff which surrounds a patient's arm during a blood pressure measurement, comprising:
   two braces having bottom surfaces to serve as a base for the sling;
   two linking members having ends which are attached to said braces so that said linking members extend between said braces; and
   two supporting straps, attached to and extending between said two linking members, for supporting the patient's arm, said straps positioned adjacent said braces so that a gap is provided between said straps for placement of the inflatable cuff such that the inflatable cuff does not touch said straps, said linking members, or external objects.

3. The sling of claim 2, wherein said supporting straps are made of a flexible material to comfortably support the patient's arm.

4. The sling of claim 2, wherein said two linking members are telescoping members which adjust to vary the size of said gap so as to accommodate patients' arms of various sizes.

5. The sling of claim 4, wherein said telescoping members are telescoping rods having circular cross sections.

6. The sling of claim 5, wherein each said telescoping rod comprises:
   a rod; and
   a hollow cylindrical tube encircling said rod, said tube sliding along said rod for adjustment of the size of said gap so as to accommodate a patient's arm.

7. The sling of claim 2, wherein bottom surfaces of the braces are covered with a shock-absorbing material to help keep the patient's arm steady during blood pressure monitoring.

8. The sling of claim 7 further comprising:
   two additional linking members located beneath said two linking members and having ends which are attached to said braces so that said two additional linking members extend between said braces; and
   shock-absorbing material located underneath and attached to said two additional linking members to help keep the patient's arm steady during blood pressure monitoring.

9. The sling of claim 2, wherein said braces are made of a foam material.

10. The sling of claim 2, wherein said supporting straps further comprise extensions so that said straps completely surround the patient's arm to help immobilize the patient's arm.

11. The sling of claim 10, wherein the extensions on said supporting straps further comprise attaching means to enclose the patient's arm in said straps.

12. A sling for use with a noninvasive blood pressure monitor to minimize contact by external objects with an inflatable cuff which surrounds a patient's arm during a blood pressure measurement, comprising:
   two supporting members which serve as bases for the sling and as supports for the patient's arm, said supporting members positioned so that a gap is provided between said supporting members for placement of the inflatable cuff such that the inflatable cuff does not touch said supporting members or said external objects; and
   at least one linking member having ends which are attached to said supporting members so that said at least one linking member extends between said supporting members.

13. The sling of claim 12, wherein said supporting members comprise blocks of a foam material.

14. The sling of claim 13, wherein said blocks and said at least one linking member are made of one integral piece of foam material.

15. The sling of claim 12, wherein said at least one linking member comprises at least two telescoping rods which may be adjusted to vary the size of said gap for accommodating a patient's arm.

16. A method of measuring blood pressure of a patient using a noninvasive blood pressure monitor and a sling to minimize contact by external objects with an inflatable cuff which surrounds the patient's arm, the sling comprising an arm rest having supporting straps for supporting the patient's limb at at least two locations so as to define an unsupported space therebetween adapted to accept the inflatable cuff such that the inflatable cuff does not touch the straps or external objects, the method comprising the steps of:

a) resting the patient's arm on the sling so that an upper portion of the patient's arm is situated in the unsupported space free from contact with the sling;

b) applying the inflatable cuff on the upper portion of the patient's arm so that the inflatable cuff does not touch the straps or external objects; and c) taking blood pressure measurements.

\* \* \* \* \*